United States Patent
Hoyt et al.

(10) Patent No.: US 7,859,256 B1
(45) Date of Patent: Dec. 28, 2010

(54) DEFECT DISCRIMINATOR FOR IN-LINE INSPECTION TOOL

(75) Inventors: Philip M. Hoyt, Murray, UT (US); Arthur K. Fox, Murray, UT (US)

(73) Assignee: Electromechanical Technologies, Inc., Murray, UT (US)

( * ) Notice: Subject to any disclaimer, the term of this patent is extended or adjusted under 35 U.S.C. 154(b) by 0 days.

(21) Appl. No.: 12/781,637

(22) Filed: May 17, 2010

Related U.S. Application Data (63) Continuation-in-part of application No. 12/269,875, filed on Nov. 12, 2008.

(51) Int. Cl.
*G01R 33/12* (2006.01)

(52) U.S. Cl. .................................... 324/220

(58) Field of Classification Search ............... 324/219, 324/220, 221
See application file for complete search history.

(56) References Cited

U.S. PATENT DOCUMENTS

| | | | |
|---|---|---|---|
| 3,335,383 A | 8/1967 | Jorden | |
| 3,373,391 A | 3/1968 | Bohm et al. | |
| 3,529,236 A * | 9/1970 | Proctor | 324/260 |
| 3,949,292 A | 4/1976 | Beaver et al. | |
| 3,967,194 A | 6/1976 | Beaver et al. | |
| 4,522,790 A | 6/1985 | Dantzig et al. | |
| 4,587,509 A | 5/1986 | Pitt et al. | |
| 4,692,703 A | 9/1987 | Extance et al. | |
| 5,293,117 A * | 3/1994 | Hwang | 324/220 |
| 5,864,232 A * | 1/1999 | Laursen | 324/220 |
| 5,942,895 A * | 8/1999 | Popovic et al. | 324/251 |
| 6,501,268 B1 | 12/2002 | Edelstein et al. | |
| 6,545,462 B2 | 4/2003 | Schott et al. | |
| 6,707,183 B2 | 3/2004 | Breynaert et al. | |
| 6,720,855 B2 | 4/2004 | Vicci | |
| 6,724,652 B2 | 4/2004 | Deak | |
| 6,847,207 B1 * | 1/2005 | Veach et al. | 324/220 |
| 6,914,805 B2 | 7/2005 | Witcraft et al. | |
| 7,015,874 B2 | 3/2006 | Ikramov et al. | |
| 7,112,957 B2 | 9/2006 | Bicking | |
| 7,256,576 B2 | 8/2007 | Mandziuk et al. | |
| 2006/0202685 A1 * | 9/2006 | Barolak et al. | 324/221 |

* cited by examiner

*Primary Examiner*—Kenneth J Whittington
(74) *Attorney, Agent, or Firm*—Warren M. Pate, LLC (57) ABSTRACT

An in-line inspection tool comprising primary and secondary sensor suites is disclosed. The primary sensor suite may detect both interior and exterior defects. The secondary sensor suite may comprise a plurality of housings distributed in the circumferential direction around the body of the tool. Each housing may contain at least one flux sensor and at least one flux concentrator. The flux concentrator may increase the flux delivered to the flux sensor, thereby increasing the sensitivity of the secondary sensor suite while reducing the number of flux sensors required. The secondary sensor suite may detect substantially exclusively interior defects. By comparing the outputs of the primary and secondary sensor suites, a user may determine whether a defect is located on the interior or exterior of a pipeline being inspected.

20 Claims, 9 Drawing Sheets

DEFECT DISCRIMINATOR FOR IN-LINE INSPECTION TOOL

RELATED APPLICATIONS

This application is a continuation-in-part of U.S. patent application Ser. No. 12/269,875 filed Nov. 12, 2008.

BACKGROUND

1. Field of the Invention

This invention relates to pipeline inspection tools, and more particularly to apparatus and methods for determining whether a defect resides on the interior or exterior surface of a pipeline.

2. Background of the Invention

Oil, petroleum products, natural gas, hazardous liquids, and the like are often transported using pipelines. The majority of these pipelines are constructed from steel pipe. Once installed, a pipeline will inevitably corrode or otherwise degrade. Proper pipeline management requires identification, monitoring, and repair of defects and vulnerabilities of the pipeline. For example, information collected about the condition of a pipeline may be used to determine safe operating pressures, facilitate repair, schedule replacement, and the like.

Typical defects of a pipeline may include corrosion, gouges, dents, and the like. Corrosion may cause pitting or general wall loss, thereby lowering the maximum operating pressure of the pipeline. Vulnerabilities may also include curvature and bending anomalies, which may lead to buckling, and combined stress and chemical or biological action such as stress corrosion cracking. Without detection and preemptive action, all such defects and vulnerabilities may lead to pipeline failure.

Information on the condition of a pipeline is often collected using an in-line inspection tool. An in-line inspection tool typically uses sensors to collect information about a pipeline as it travels therethrough. In the past, in-line inspection tools have used magnetic flux leakage to determine the condition of a pipeline wall. Flaws in ferromagnetic pipe can be detected by the perturbations they cause in a magnetic field applied to the wall of a pipeline.

Some in-line inspection tools include primary sensors suitable to identify defects that occur in ferromagnetic pipe both on the inner diameter (ID) or interior surface and on the outer diameter (OD) or exterior surface of the pipe. However, the primary sensors may be unable to determine which are interior defects (i.e., located on the inner diameter) and which are exterior defects (i.e., located on the outer diameter). Accordingly, some in-line inspection tools include secondary sensors tasked with discriminating between interior and exterior defects.

Current technologies require numerous secondary sensors, usually about half the number of primary sensors. Accordingly, current systems are hampered by the cost, power consumption, space consumption, data storage consumption of all those secondary sensors. Thus, what is needed is a new apparatus and method for reducing the number of secondary sensors without reducing the ability to discriminate between interior and exterior defects.

SUMMARY

An in-line inspection tool and associated methods in accordance with the present invention may comprise or utilize various components including a plurality of inspection assemblies. The inspection assemblies may be distributed circumferentially about the tool. Inspection assemblies may move in a radial direction with respect to the main body of an in-line inspection tool. This freedom of motion may accommodate general and local changes in the pipeline being inspected.

In selected embodiments, an inspection assembly may include a sensor assembly and a mount. A mount may extend to connect a sensor assembly to the rest of an in-line inspection tool. A mount may enable a sensor assembly to move in a radial direction with respect to the rest of an in-line inspection tool. In certain embodiments, a mount may comprise a four bar linkage (e.g., a parallelogram linkage). A mount may hold a sensor assembly in a proper orientation against the interior surface of the pipeline being inspected.

A sensor assembly may include a housing, circuit board assembly, back bar, two magnets, one or more sensors (e.g., flux sensors), one or more flux concentrators, two fillers, and a wear plate. The housing may contain and protect other components of a sensor assembly from the pressure and chemicals found in a pipeline environment. A circuit board assembly may include whatever electronic components or connections are necessary to support proper operation of the one or more sensors connected thereto.

A back bar may be formed of a magnetic material and form a link in the magnetic circuit of a sensor assembly. The two magnets may have opposite polarity and be positioned on a back bar, one opposite the other. The magnets may generate a magnetic field thereabout. Two fillers, one for each magnet, may be formed of a material (e.g., low carbon steel) suitable for passing or conducting the magnetic field from the magnets to the face of the sensor assembly. Accordingly, with the face of the sensor assembly positioned directly against the interior surface of a pipeline, the interior surface, fillers, magnets, and back bar may combine to form a magnetic circuit.

Extending between the two magnets to effectively form a small short in the magnetic circuit may be a combination of one or more sensors and one or more flux concentrators. Accordingly, when a defect in the wall of a pipeline perturbs the magnetic field applied thereto by a sensor assembly, that perturbation may be directed by one or more of the flux concentrators to one or more corresponding sensors. Accordingly, defects (i.e., interior defects) in the pipe wall anywhere across the width of the sensor assembly (and slightly therebeyond) may be detected.

In operation, a primary sensor suite may detect both interior and exterior defects. In contrast, due to the size or type of the magnets involved, the magnetic field induced into the wall of a pipe by the secondary sensor suite may be weak. This weak magnetic field may not penetrate to the outside of the pipeline being inspected. Thus, the magnetic field generated by a secondary sensor suite may be altered (i.e., perturbed) by interior defects, but not by exterior defects.

By so limiting a secondary sensor suite, an inference may be made that if the primary sensor suite detects a defect, but the secondary sensor suite does not, then the defect must be located on the exterior of the pipeline being inspected. Conversely, if both the primary and secondary sensor suites detect a defect, then the defect must be located on the interior of the pipeline being inspected.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention as claimed, but is merely representative of various embodiments of the invention. The illustrated embodiments of the invention will be best understood by reference to the drawings, wherein like parts are designated by like numerals throughout.

Figure 1:
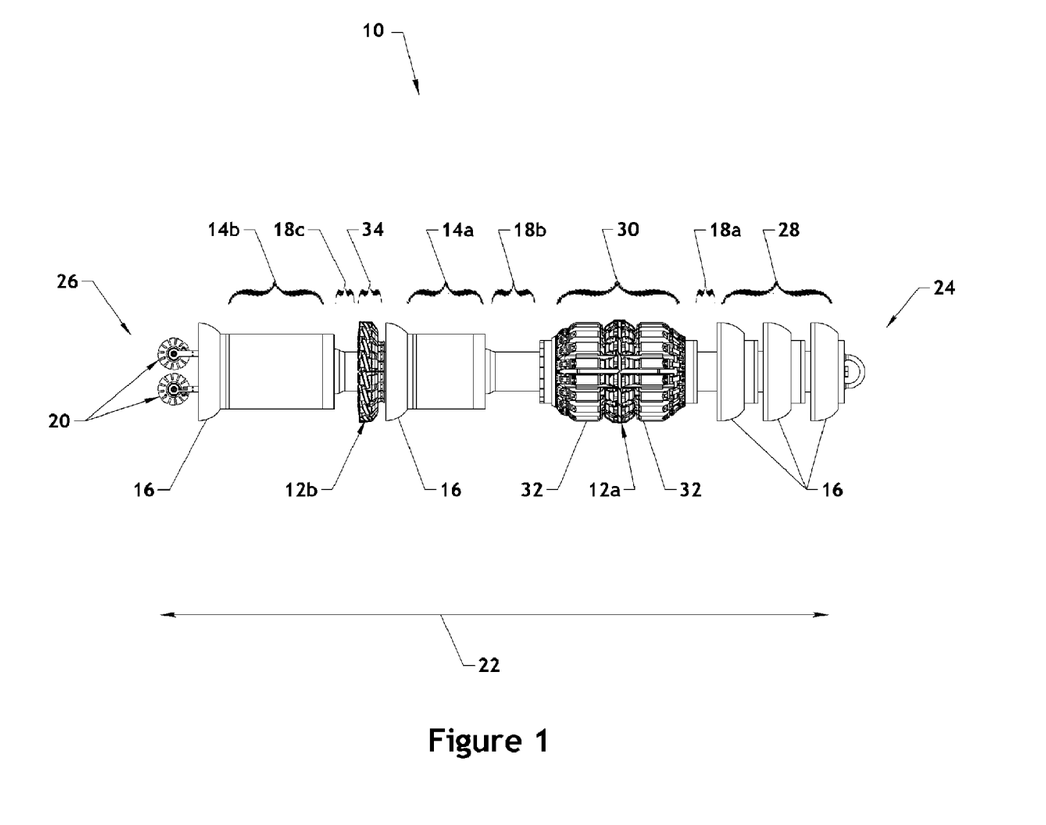
FIG. 1 is an elevation view of one embodiment of an in-line inspection tool in accordance with the present invention.

Referring to FIG. 1, an in-line inspection tool 10 or vehicle 10 in accordance with the present invention may comprise various components including inspection sensors 12a, 12b, canisters 14, driving cups 16, couplers 18, position sensors 20, and the like. Depending on the configuration of the in-line inspection tool 10 and the size of the pipeline to be inspected, the arrangement and number of components (e.g., the number of canisters 14) may vary.

Canisters 14 may house equipment such as one or more processors, memory devices, and batteries. The driving cups 16 may center the tool 10 within the pipeline and enable fluid traveling within a pipeline to engage the tool 10, thereby pushing the tool 10 through the pipeline. In selected embodiments, driving cups 16 may be formed of a somewhat flexible polyurethane or similar material. Couplers 18 may support bending of the tool 10, enabling the tool 10 to accommodate bends in the pipeline. Like the driving cups 16, in selected embodiments the couplers 18 may be formed of somewhat flexible polyurethane or similar material. Alternatively, the couplers 18 may be formed of a mechanical pivoting device.

An in-line inspection tool 10 may extend in a longitudinal direction 22 from a head end 24 to a tail end 26. The various components 12, 14, 16, 18, 20 of an in-line inspection tool 10 may be arranged in series. For example, in the illustrated embodiment, the head end 24 of a tool 10 may comprise a head section 28 comprising one or more driving cups 16. Following the head section 28 may be a primary sensor suite 30. In selected embodiments, a primary sensor suite 30 may comprise an array of magnets 32 and sensors 12a. A coupler 18a may extend to connect the head section 28 to the primary sensor suite 30.

Following the primary sensor suite 30 may be a first canister 14a. In one embodiment, the first canister 14a may house the hardware providing the processing and memory storage for the in-line inspection tool 10. A coupler 18b may extend to connect the primary sensor suite 30 to the first canister 14a.

The first canister 14a may be followed by another driving cup 16 and a secondary sensor suite 34. A coupler 18c may engage the second sensor suite 34 and extend rearwardly to engage a second canister 14b. In one embodiment, the second canister 14b may house the batteries providing the power for the in-line inspection tool 10.

In selected embodiments, a driving cup 16 may connect to the second canister 14b. One or more position sensors 20 may then engage the second canister 14b, driving cup 16, or some combination thereof to form the tail end 26 of the in-line inspection tool 10. In one embodiment, the position sensors 20 may comprise one or more odometers 20 positioned to roll along the interior surface of the pipeline and measure the distance traveled by the in-line inspection tool 10.

Figure 2:
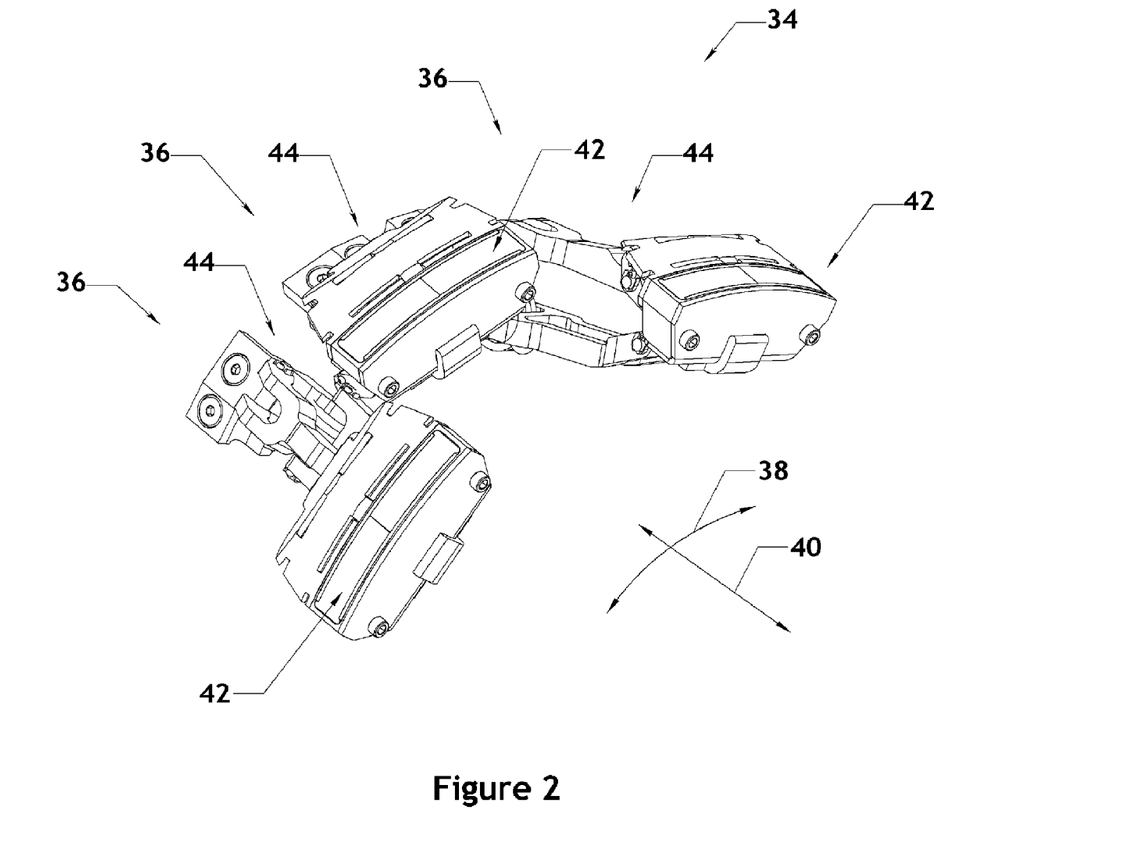
FIG. 2 is a perspective view of selected inspection assemblies positioned with respect to one another as they would be when installed on an in-line inspection tool in accordance with the present invention.

Referring to FIG. 2, in selected embodiments, a secondary sensor suite 34 may include a plurality of inspection assemblies 36 distributed circumferentially (i.e., in a circumferential direction 38) about a central axis 40 of an in-line inspection tool 10. Each inspection assembly 36 may include a sensor assembly 42 and a mount 44. A mount 44 may extend to connect a sensor assembly 42 to the rest of an in-line inspection tool 10. For example, a mount 44 may extend to connect corresponding sensor assembly 42 to an interior cylinder (not shown) forming the back bone of the secondary sensor suite 34. Accordingly, inspection assemblies 36 may encircle the interior cylinder.

In selected embodiments, sensor assemblies 42 may be staggered in the axial direction 40. Accordingly, as adjacent sensor assemblies 42 move inward in a radial direction, they may do so without structural interference therebetween. This stagger may be accomplished by shortening the length of every other mount 44. Alternatively, the stagger may be accomplished by alternating in the axial direction 40 the position of securement between the mounts 44 and the rest of an in-line inspection tool 10.

In certain alternative embodiments, sensor assemblies 42 may be shaped and secured in the manner described in U.S. patent application Ser. No. 12/403,754 filed Mar. 13, 2009, which is hereby incorporated by reference. Accordingly, sensor assemblies 42 in accordance with the present invention may be held adjacent to one another with the first end of one sensor assembly 42 circumferentially overlapping the second end of an adjacent sensor assembly 42. For example, a first end of each sensor assembly 42 may be tapered toward the leading edge of the sensor assembly 42. The second end of each sensor assembly 42 may be tapered toward the trailing edge thereof.

As adjacent sensor assemblies 42 move inward in a radial direction, they may be urged closer to one another. The force urging the two sensor assemblies 42 closer together may increase the overlap thereof. In selected embodiments, the abutting surfaces may be specifically designed to permit or even facilitate this additional overlap.

With additional overlap of adjacent sensor assemblies 42, each sensor assembly 42 may tend to rotate about an axis extending in the radial direction. That is, for sensor assemblies 42 to slide past one another, each sensor assembly 42 may rotate to vacate space into which an adjacent sensor assembly 42 may extend. The corresponding angles or tapers of adjacent contacting ends may ensure that each sensor assembly 42 rotates in the same direction. While overlap of sensor assemblies 42 may result in multiple sensors tracking the same portion of pipe, this redundancy in constricted spaces may ensure that sensor coverage in non-constricted spaces is uniformly distributed and complete.

In selected embodiments, a mount 44 may be sufficiently flexible or provide a pivoting mechanism to permit a sensor assembly 42 held thereby to rotate about an axis extending in the radial direction in the manner described hereinabove. A mount 44 may also be sufficiently biased so that after the constriction in the pipe has passed, the mount 44 may return the sensor assembly 42 held thereby to its original alignment.

Figure 3:
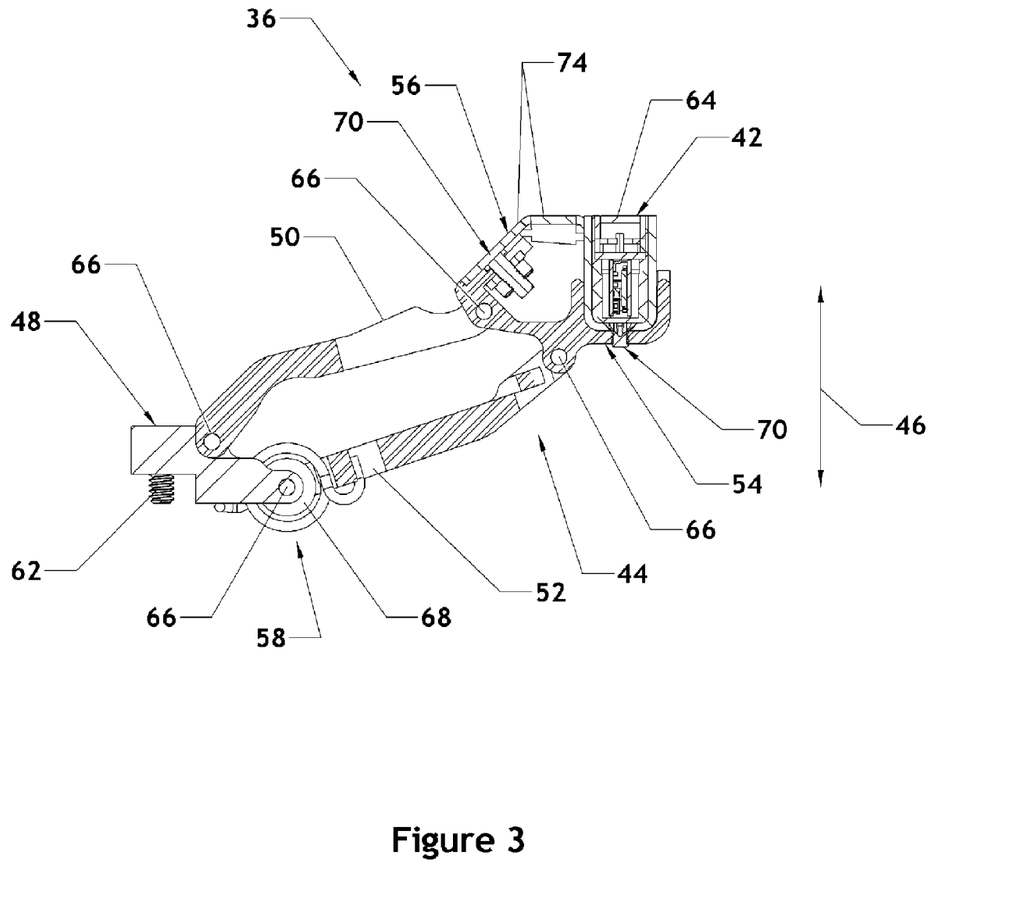
FIG. 3 is a cross-sectional view of one embodiment of an inspection assembly in accordance with the present invention.
Figure 4:
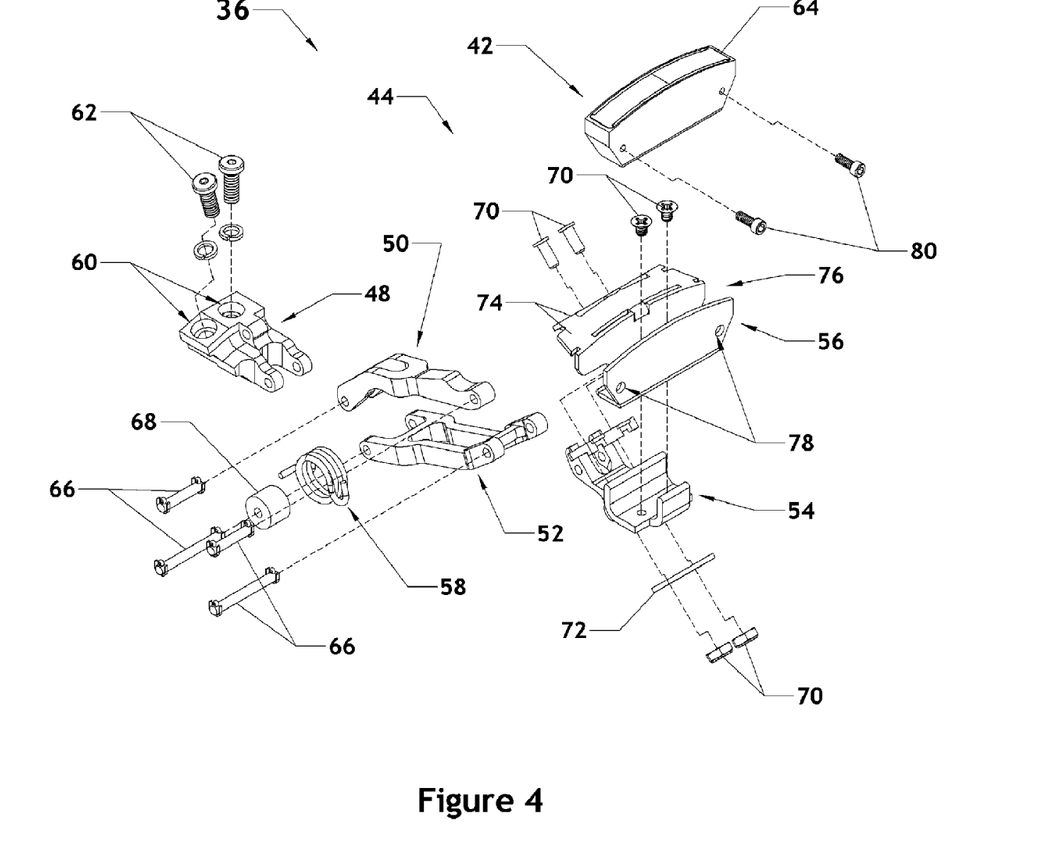
FIG. 4 is an exploded perspective view of the inspection assembly of FIG. 3.

Referring to FIGS. 3 and 4, inspection assemblies 36 may move with respect to the interior cylinder or main body of an in-line inspection tool 10. For example, a mount 44 of an inspection assembly 36 may enable a sensor assembly 42 to move in a radial direction 46 with respect to the rest of an in-line inspection tool 10. This freedom of motion may accommodate changes in the pipe being inspected. For example, features such as bends, constrictions, changes in the thickness of the wall of the pipe, circumferential welds, dents, and damaged pipe walls may all affect the interior diameter of a pipeline. Movement of mounts 44 may permit corresponding sensor assemblies 42 to closely track the interior surface of a pipeline in spite of changes in the interior diameter thereof.

In selected embodiments, a mount 44 in accordance with the present invention may include a base 48, first link 50, second link 52, interface 54, wear plate 56, and biasing member 58. A base 48 may include one or more apertures 60 for receiving fasteners 62. The fasteners 62 may provide the connection between a corresponding inspection assembly 36 and the rest of an in-line inspection tool 10.

In operation, a base 48, first link 50, second link 52, and interface 54 may operate as a four bar linkage. For example, a base 48, first link 50, second link 52, and interface 54 may form a parallelogram linkage. Accordingly, the base 48, first link 50, second link 52, and interface 54 may hold a sensor assembly 42 in the correct location against the interior surface of the pipeline being inspected, restrict movement of the sensor assembly 42 to a single radial plane (i.e., a plane containing the central axis 40), and support movement of the sensor assembly 42 within the radial plane to pass bends, changes in diameter, pipeline features, and damaged pipe walls without impeding movement of the in-inspection tool 10. In selected embodiments, various pins 66 may pivotably connect the base 48, first link 50, second link 52, and interface 54 to another.

A biasing member 58 may urge or bias a mount 44 to a particular location within its range of motion. For example, a biasing member 58 may urge a parallelogram linkage formed by a base 48, first link 50, second link 52, and interface 54 radially outward to one extreme of its range of motion. Accordingly, a biasing member 58 may hold a sensor assembly 42 against the interior surface of the pipeline being inspected, despite gravitational forces, magnetic forces, and the like that may urge the sensor assembly 42 toward the central axis 40 of the in-line inspection tool 10.

In selected embodiments, a biasing member 58 may be configured as a torsion spring. For example, in the illustrated embodiment, a biasing member 58 is configured as a torsion spring and held in place about a pivot pin 66 by a spring spacer 68. The torsion spring has a first end engaging a base 48 and a second end engaging a second link 52. Accordingly, pivoting of the second link 52 with respect to the base 48 may respectively load and unload the torsion spring. If desired or necessary, a torsion spring may be preloaded such that there is an immediate and significant resistance to inward deflection of a corresponding sensor assembly 42.

An interface 54 may provide a location for securing a wear plate 56 to the rest of a mount 44. In certain embodiments, an interface 54 may include various fasteners 70 securing a wear plate 56 thereto. In selected embodiments, the various fasteners 70 may include two threaded fasteners 70 welded to extend from the underside of a wear plate 56 (e.g., below one of the wear surfaces 74). Washers 72 and the like may be included as needed or desired to effect a proper and secure connection between an interface 54 and a wear plate 56. In certain alternative embodiments, an interface 54 may support pivoting of a sensor assembly 42 about an axis extending in a radial direction 46, facilitating the overlap described hereinabove.

A wear plate 56 may include various wear surfaces 74. The wear surfaces 74 may be positioned to slide along the interior surface of a pipeline during inspection. Accordingly, a wear plate 56 may be configured to withstand such use. Moreover, a wear plate 56 may prevent other components of an inspection assembly 36 from being exposed to such wear.

In selected embodiments, a wear plate 56 may include a cradle 76. A cradle 76 may be sized and shaped to receive a sensor assembly 42 therewithin. A cradle 76 may also be configured to retain a sensor assembly 42 therewithin. For example, in certain embodiments, a cradle 76 may include one or more apertures 78 for receiving fasteners 80. Accordingly, the fasteners 78 may pass through the apertures 78 and engage a sensor assembly 42, thereby securing the sensor assembly 42 to the wear plate 56 and to the rest of the inspection assembly 36.

Figure 5:
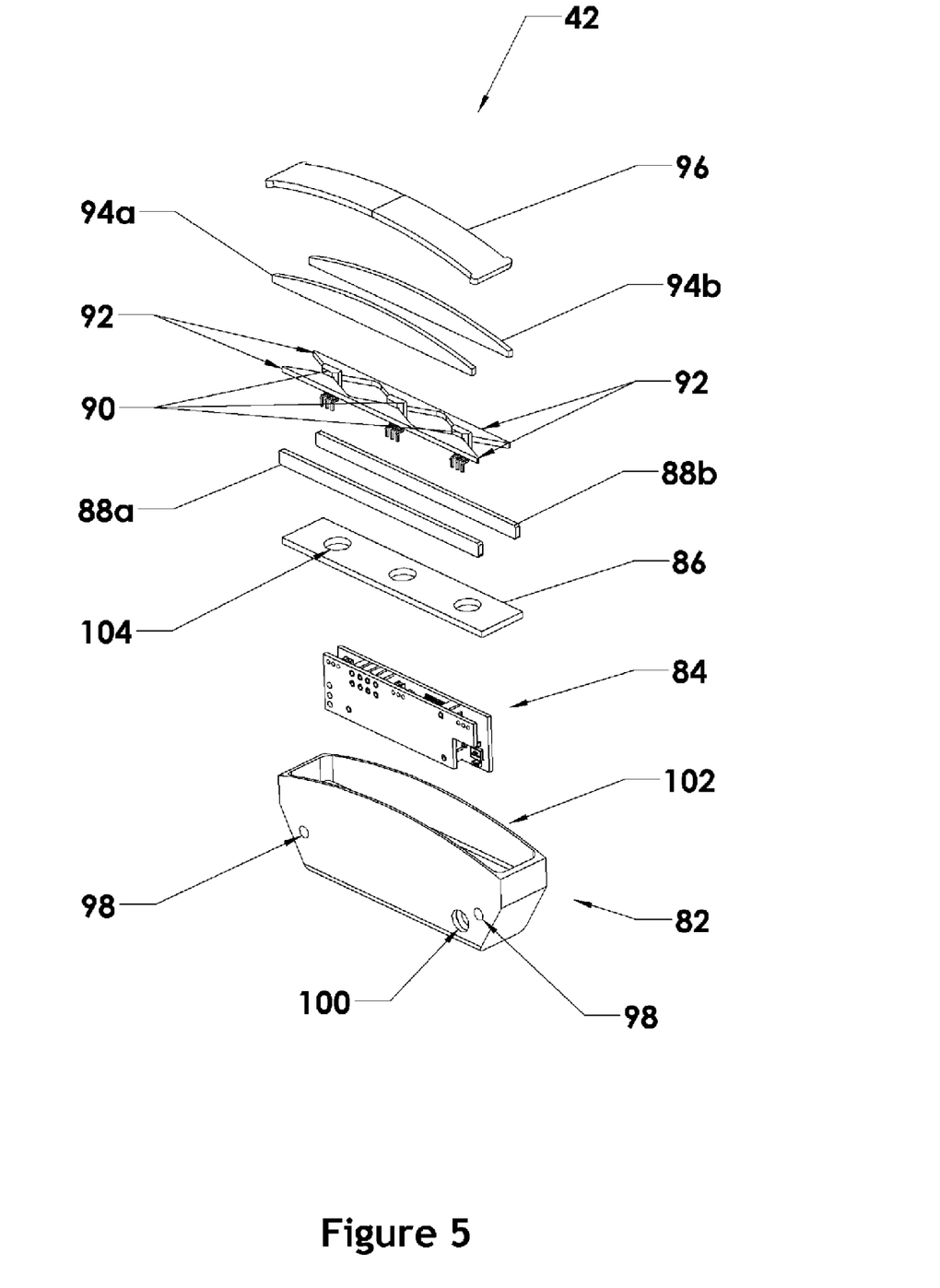
FIG. 5 is an exploded perspective view of one embodiment of a sensor assembly in accordance with the present invention.
Figure 6:
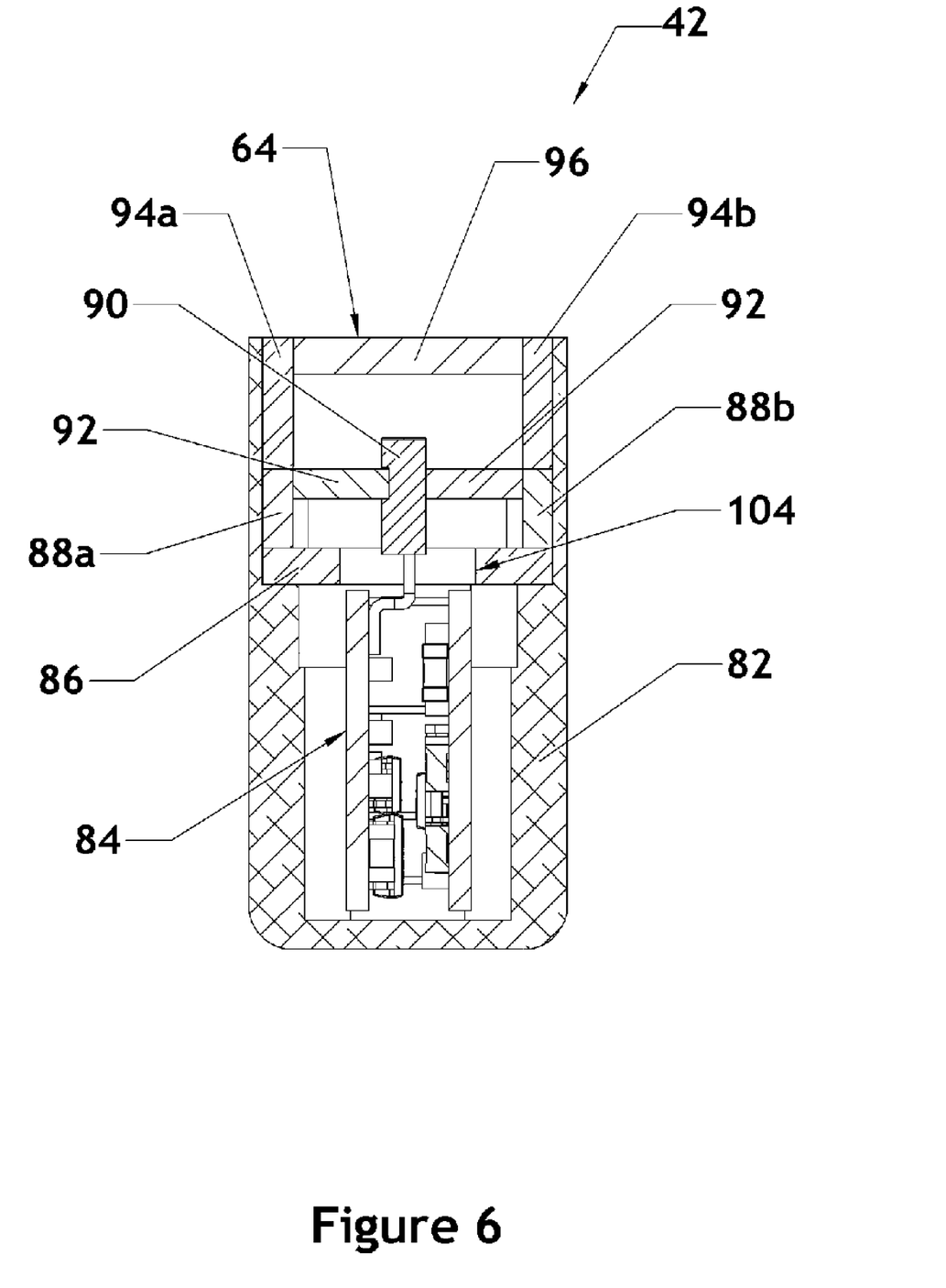
FIG. 6 is a cross-sectional view of the sensor assembly of FIG. 5.

Referring to FIGS. 5 and 6, in certain embodiments, a sensor assembly 42 in accordance with the present invention may include a housing 82, circuit board assembly 84, back bar 86, two magnets 88a, 88b, one or more sensors 90 (e.g., flux sensors 90), one or more flux concentrators 92, two fillers 94a, 94b, and a wear plate 96. A housing 82 may contain and protect other components of a sensor assembly 42 from the pressure and chemicals found in a pipeline environment. In selected embodiments, one or more of the components within a housing 82 may be potted in chemical and pressure resistant materials (e.g., selected polymers).

A housing 82 may include various apertures 98, 100, 102. One or more such apertures 98 may receive fasteners 80 for securing a sensor assembly 42 in place. Another aperture 100 may provide a location for wires to exit or enter the housing 82. Yet another aperture 102 may provide the opening into which the other components of a sensor assembly 42 are inserted during a manufacturing or installation process.

A circuit board assembly 84 in accordance with the present invention may include whatever electronic components or connections are necessary to support proper operation of the one or more sensors 90 connected thereto. A back bar 86 may be formed of a magnetic material and form a link in the magnetic circuit of a sensor assembly 42. In selected embodiments, a back bar 88 may include one or more apertures 104 extending therethrough. The apertures 104 may enable sensors 90 positioned on one side of a back bar 86 to connect to a circuit board assembly 84 positioned on an opposite side of the back bar 86.

In selected embodiments, two magnets 88*a*, 88*b* of opposite polarity may be positioned on a back bar 86, one opposite the other. In such embodiments, the magnets 88*a*, 88*b* may generate a magnetic field thereabout. Fillers 94*a*, 94*b*, one for each magnet 88*a*, 88*b*, may be formed of a material (e.g., low carbon steel) suitable for passing or conducting the magnetic field from the magnets 88 to the face 64 of the sensor assembly 42. Accordingly, with the face 64 of the sensor assembly 42 positioned directly against the interior surface of a pipeline, the interior surface, the fillers 94, magnets 88, and back bar 86 may combine to form a magnetic circuit.

Extending between the two magnets 88*a*, 88*b* to effectively form a small short in the magnetic circuit may be a combination of one or more sensors 90 and one or more flux concentrators 92. The one or more sensors 90 may monitor the magnetic circuit or field for perturbations thereof.

In operation, a primary sensor suite 30 may detect both interior and exterior defects. In contrast, due to the size or type of the magnets 88 involved, the magnetic field induced into the wall of a pipe by the secondary sensor suite 34 may be weak. This weak magnetic field may not penetrate to the outside of the pipeline being inspected. Thus, the magnetic field generated by a secondary sensor suite 34 may be altered (i.e., perturbed) by interior defects, but not by exterior defects.

By so limiting a secondary sensor suite 34, an inference may be made that if the primary sensor suite 30 detects a defect, but the secondary sensor suite 34 does not, then the defect must be located on the exterior of the pipeline being inspected. Conversely, if both the primary and secondary sensor suites 30, 34 detect a defect, then the defect must be located on the interior of the pipeline being inspected.

Capping a housing 82 may be a wear plate 96. A wear plate 96 may be formed of a non-magnetic, wear-resistant material. For example, a wear plate 96 may be formed of a non-magnetic alloy of select metals. In selected embodiments, a wear plate 96 may be arced to match the curvature of the interior surface of a pipeline to be inspected. The fillers 94 may be similarly arced. Accordingly, a sensor assembly 42 may be configured at its face 64 to support intimate contact with the interior surface of the pipeline.

Select components of an inspection assembly 36 may be formed of non-magnetic, minimally magnetic, or magnetically permeable materials. For example, certain components may be formed of non-magnetic stainless steel. This may preclude or limit the undesirable interference of such components with the magnetic field induced in the wall of the pipe being inspected.

Figure 7:
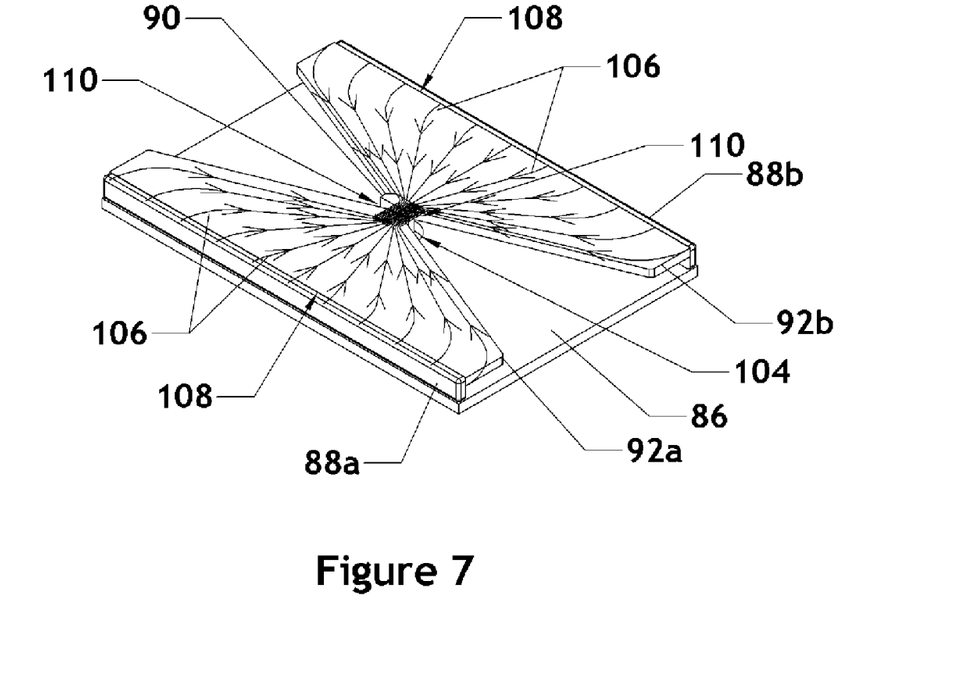
FIG. 7 is a schematic perspective view of a sensor, flux concentrator pair, magnet pair, and back bar in accordance with the present invention.
Figure 8:
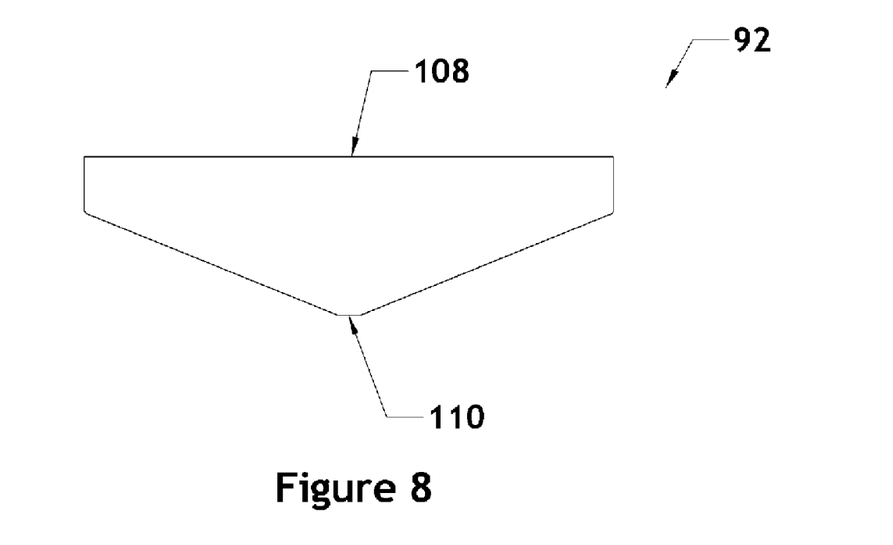
FIG. 8 is a schematic top plan view of one embodiment of a flux concentrator in accordance with the present invention.

Referring to FIGS. 7 and 8, flux concentrators 92 in accordance with the present invention may strengthen the magnetic flux 106 delivered to a sensor 90 (e.g., flux sensor 90). In selected embodiments, a flux concentrator 92 may be formed of a material with higher magnetic permeability than the surrounding matter (e.g., air, potting material, or the like). A flux concentrator 92 may have a relatively wide distal end 108 or edge 108 and a relatively narrow proximal end 110 or edge 110. A flux concentrator 92 may further include a gradual taper creating a smooth transition from the distal end 108 to the proximal end 110.

In operation, due to its higher magnetic permeability, a flux concentrator 92 or pair of flux concentrators 92*a*, 92*b* may create a short in the magnetic circuit or field generated by corresponding, adjacent magnets 88*a*, 88*b*. Accordingly, flux 106 may be routed in a first concentrator 92*b* and concentrated at the narrow end 110 thereof, proximate a flux sensor 90. The flux sensor 90 may measure the strength of the concentrated magnetic field more readily than the strength of the lower level ambient field As flux 106 passes through a sensor 90, it may exit adjacent a narrow edge 110 of a second flux concentrator 92*a*. The second flux concentrator 92*a* may provide continuity to the concentrated flux field and return the concentrated field to the normal level in the ambient background field. Accordingly, one flux concentrator 92*b* may fulfill the concentration role, while the other 92*a* guides the concentrated flux field through the flux sensor 90, receives the concentrated flux field, and distributes the flux field back to its original dimensions.

Figure 9:
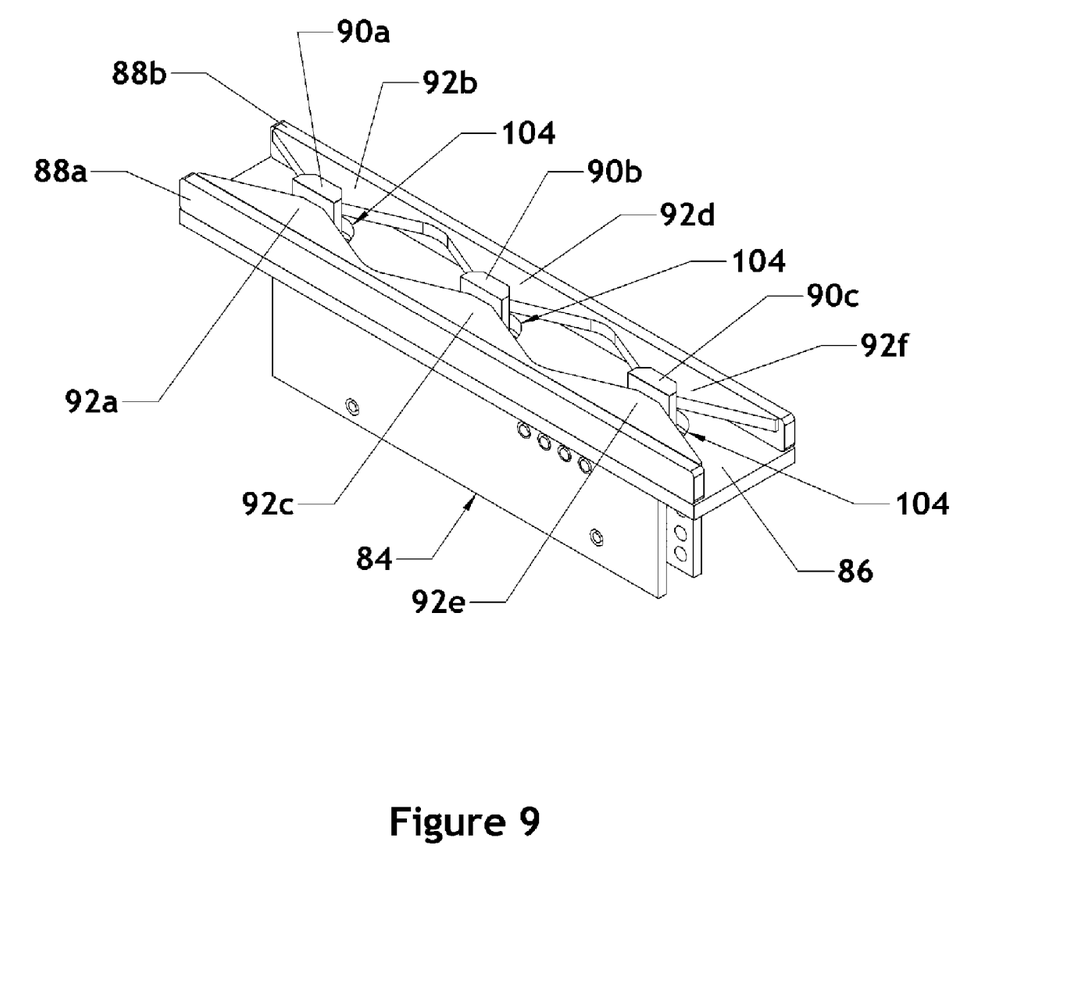
FIG. 9 is a perspective view of selected internals of a multi-sensor embodiment of a sensor assembly in accordance with the present invention.

Referring to FIG. 9, in selected embodiments, a sensor assembly 42 may include more than one sensor 90. For example, in the illustrated embodiment, a sensor assembly 42 includes three flux sensors 90*a*, 90*b*, 90*c*. Each flux sensor 90 may be positioned between two flux concentrators 92, each positioned as a minor image of the other. For example, a first flux sensor 90*a* may be positioned between first and second flux concentrators 92*a*, 92*b*, a second flux sensor 90*b* may be positioned between third and fourth flux concentrators 92*c*, 92*d*, and a third flux sensor 90*c* may be positioned between fifth and sixth flux concentrators 92*e*, 92*f*.

When an interior defect in the wall of a pipe perturbs the magnetic field applied thereto by a sensor assembly 42, that perturbation may be directed by one or more of the flux concentrators 92 to one or more of the flux sensors 90. Accordingly, defects in the pipe wall anywhere across the width of the sensor assembly 42 (and slightly therebeyond) may be detected. In certain embodiments comprising a sensor assembly 42 with multiple sensors 90, those multiple sensors 90 may be connected in series on a single circuit. Accordingly, in such embodiments, any change in the magnetic field caused by a defect anywhere across the width of the sensor assembly 42 may be passed along a single data line and a single recording channel. Thus, a sensor assembly 42 may be very sensitive, yet conserve data storage space.

Figure 10:
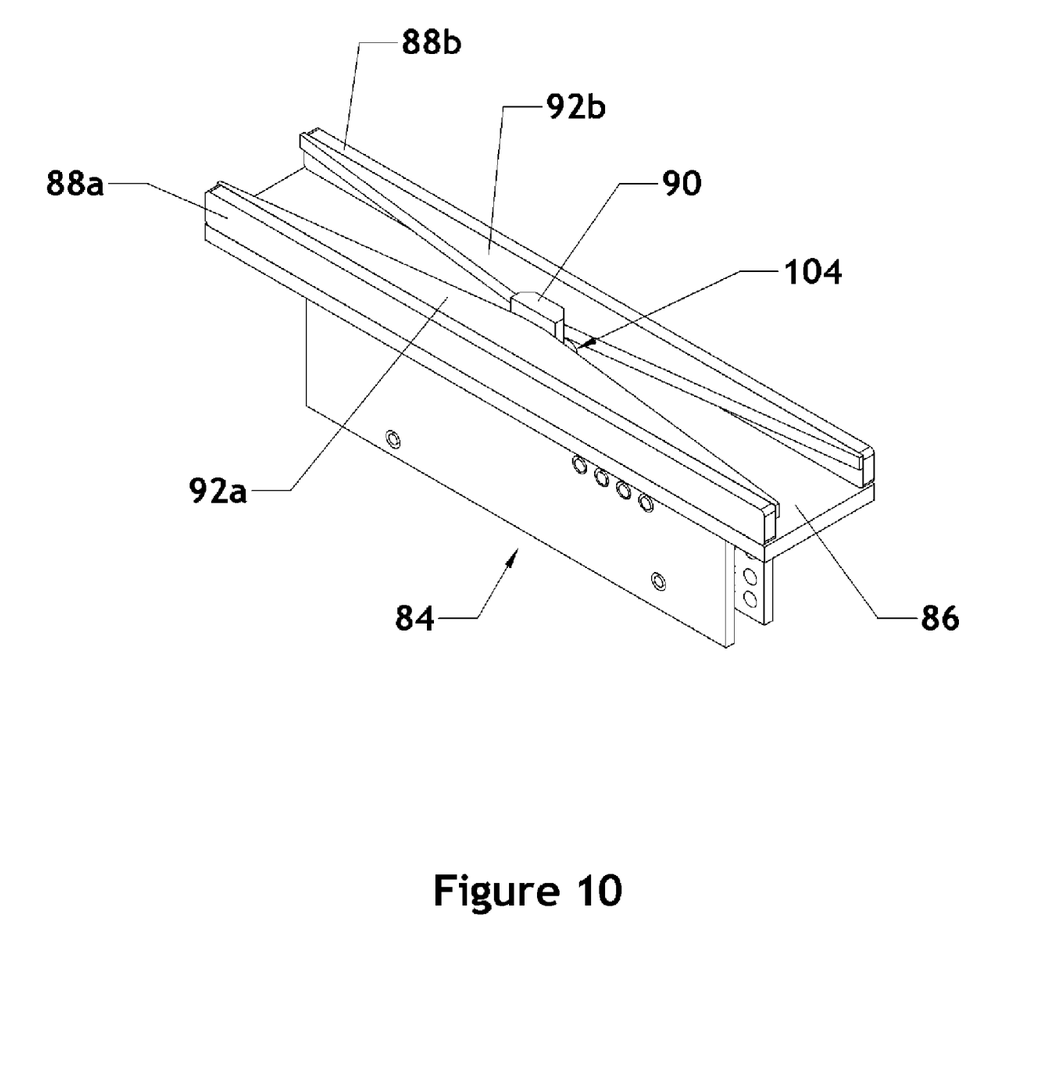
FIG. 10 is a perspective view of selected internals of a single-sensor embodiment of a sensor assembly in accordance with the present invention.

Referring to FIG. 10, in selected embodiments, a sensor assembly 42 may include only one sensor 90. For example, in the illustrated embodiment, a sensor assembly 42 includes one flux sensor 90. This one flux sensor 90 may be positioned between two flux concentrators 92*a*, 92*b*, each positioned as a mirror image of the other. Accordingly, when an interior defect in the wall of a pipe perturbs the magnetic field applied thereto by a corresponding sensor assembly 42, that perturbation may be directed by a flux concentrator 92 to the flux sensor 90. Accordingly, defects in the pipe wall anywhere across the width of the sensor assembly (and slightly therebeyond) may be detected. Thus, a sensor assembly 42 may be sufficiently sensitive, yet save the cost of additional sensors and conserve electrical power.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method comprising:
   obtaining an in-line inspection tool comprising
      a body portion comprising a first segment, a second segment trailing the first segment, and at least one coupler flexibly connecting the first segment to the second segment, a primary sensor suite riding on one of the first segment and second segment, and a secondary sensor suite riding on the other of the first segment and the second segment, the secondary sensor suite comprising at least one flux sensor and at least one flux concentrator;

introducing the in-line inspection tool into a pipeline;

inspecting, by the in-line inspection tool, the pipeline;

detecting, by the primary sensor suite during the inspecting, both interior and exterior defects;

detecting, by the secondary sensor suite during the inspecting, exclusively interior defects;

receiving, by the at least one flux concentrator during the inspecting, a first magnetic flux; and delivering, by the at least one flux concentrator to the at least one flux sensor during the inspecting, a second magnetic flux, greater than the first magnetic flux.

2. The method of claim 1, wherein:

the primary sensor suite is connected to one of the first segment and the second segment via a first suspension system; and the secondary sensor suite is connected to the other of the first segment and the second segment via a second suspension system, independent of the first suspension system.

3. The method of claim 1, wherein the at least one flux concentrator comprises magnetically permeable material having a proximal edge and a distal edge positioned opposite the proximal edge, the distal edge being longer than the proximal edge.

4. The method of claim 3, wherein the proximal edge is positioned adjacent the at least one flux sensor.

5. An in-line inspection tool for inspecting a pipeline while traveling therethrough, the in-line inspection tool comprising:

a body portion defining axial and circumferential directions;

a primary sensor suite comprising a plurality of primary sensors distributed in the circumferential direction around the body portion;

the primary sensor suite connected to the body portion via a first suspension system;

the primary sensor suite operating proximate one or more primary magnetic fields having a strength selected to enable the primary sensor suite to detect both interior and exterior defects;

a secondary sensor suite comprising a plurality of housings distributed in the circumferential direction around the body portion;

the secondary sensor suite wherein each housing of the plurality of housings contains at least one flux sensor and at least one flux concentrator, the at least one flux concentrator comprising magnetically permeable material having a proximal edge, a distal edge positioned opposite the proximal edge, the distal edge longer than the proximal edge, and the proximal edge positioned adjacent the at least one flux sensor;

the secondary sensor suite connected to the body portion via a second suspension system, independent of the first suspension system; and the secondary sensor suite operating proximate one or more secondary magnetic fields having a strength selected to enable the secondary sensor suite to detect exclusively interior defects.

6. The in-line inspection tool of claim 5, wherein the second suspension system independently suspends each housing of the plurality of housings from the body portion.

7. The in-line inspection tool of claim 5, wherein:

the body portion comprises a first segment and a second segment, trailing the first segment in the axial direction;

the primary sensor suite rides on one of the first segment and the second segment; and the secondary sensor suite rides on the other of the first segment and the second segment.

8. The in-line inspection tool of claim 7, wherein at least one coupler flexibly connects the first segment to the second segment.

9. The in-line inspection tool of claim 5, wherein each housing of the plurality of housings contains a single flux sensor.

10. The in-line inspection tool of claim 9, wherein the at least one flux concentrator comprises two flux concentrators, each comprising magnetically permeable material having:

a proximal edge;

a distal edge positioned opposite the proximal edge;

the distal edge longer than the proximal edge; and the proximal edge positioned adjacent the single flux sensor.

11. The in-line inspection tool of claim 10, wherein:

each housing of the plurality of housings has a length aligned with the circumferential direction; and the distal edges of the two flux concentrators each extend a majority of the length of a corresponding housing of the plurality of housings.

12. An in-line inspection tool for inspecting a pipeline while traveling therethrough, the tool comprising:

a body portion defining an axial direction;

a primary sensor suite connected to the body portion via a first suspension system;

the primary sensor suite operating proximate one or more primary magnetic fields having a strength selected to enable the primary sensor suite to detect both interior and exterior defects;

a secondary sensor suite connected to the body portion via a second suspension system, independent of and spaced in the axial direction from the first suspension system; and the secondary sensor suite operating proximate one or more secondary magnetic fields having a strength selected to enable the secondary sensor suite to detect exclusively interior defects.

13. The tool of claim 12, wherein the secondary sensor suite comprises:

a plurality of flux sensors;

a plurality of housings, each housing of the plurality of housings containing at least one flux sensor of the plurality of flux sensors and at least one flux concentrator.

14. The tool of claim 13, wherein the at least one flux concentrator comprises magnetically permeable material having:

a proximal edge;

a distal edge positioned opposite the proximal edge;

the distal edge longer than the proximal edge, and the proximal edge positioned adjacent the at least one flux sensor.

15. The tool of claim 13, wherein each housing of the plurality of housings contains a single flux sensor.

16. The tool of claim 15, wherein the at least one flux concentrator comprises two flux concentrators, each comprising magnetically permeable material having:

a proximal edge;

a distal edge positioned opposite the proximal edge;
the distal edge longer than the proximal edge; and
the proximal edge positioned adjacent the single flux sensor.

17. The tool of claim 16, wherein:
each housing of the plurality of housings has a length aligned with the circumferential direction; and
the distal edges of the two flux concentrators each extend a majority of the length of a corresponding housing of the plurality of housings.

18. The tool of claim 12, wherein the second suspension system independently suspends each housing of the plurality of housings from the body portion.

19. The tool of claim 12, wherein:
the body portion comprises a first segment and a second segment, trailing the first segment in the axial direction;
the primary sensor suite rides on one of the first segment and the second segment; and
the secondary sensor suite rides on the other of the first segment and the second segment.

20. The tool of claim 19, wherein at least one coupler flexibly connects the first segment to the second segment.

* * * * *